United States Patent
Gochnour et al.

(10) Patent No.: US 8,920,392 B2
(45) Date of Patent: Dec. 30, 2014

(54) METHOD FOR TREATING OVERACTIVE BLADDERS AND A DEVICE FOR STORAGE AND ADMINISTRATION OF TOPICAL OXYBUTYNIN COMPOSITIONS

(75) Inventors: Scott Gochnour, Salt Lake City, UT (US); Venkatesh Subramanyan, Salt Lake City, UT (US); Michael W. Kimball, Salt Lake City, UT (US)

(73) Assignee: Watson Laboratories, Inc., Salt Lake City, UT (US)

( * ) Notice: Subject to any disclaimer, the term of this patent is extended or adjusted under 35 U.S.C. 154(b) by 693 days.

(21) Appl. No.: 12/435,895

(22) Filed: May 5, 2009

(65) Prior Publication Data

US 2010/0286630 A1    Nov. 11, 2010

(51) Int. Cl.

| | |
|---|---|
| *A61M 35/00* | (2006.01) |
| *A61K 31/216* | (2006.01) |
| *A45D 37/00* | (2006.01) |
| *A61K 9/00* | (2006.01) |
| *A61K 9/06* | (2006.01) |
| *A61K 47/38* | (2006.01) |
| *A61K 9/70* | (2006.01) |

(52) U.S. Cl.
CPC .............. *A61K 9/009* (2013.01); *A61K 31/216* (2013.01); *A45D 37/00* (2013.01); *A61K 9/0014* (2013.01); *A61K 9/06* (2013.01); *A61K 47/38* (2013.01); *A61K 9/7084* (2013.01)
USPC ............................ 604/290; 424/449; 604/289

(58) Field of Classification Search
USPC ............................ 604/289, 290; 424/443, 449
See application file for complete search history.

(56) References Cited

U.S. PATENT DOCUMENTS

| | | |
|---|---|---|
| 2,954,116 A | 9/1960 | Maso et al. |
| 2,998,880 A | 9/1961 | Ladd |
| 3,057,467 A | 10/1962 | Williams |
| 3,124,825 A | 3/1964 | Iovenko |
| 3,152,515 A | 10/1964 | Land |
| 3,152,694 A | 10/1964 | Nashed et al. |
| 3,186,869 A | 6/1965 | Friedman |
| 3,217,871 A | 11/1965 | Lee |
| 3,403,776 A | 10/1968 | Denny |
| 3,478,868 A | 11/1969 | Nerenberg et al. |
| 3,552,638 A | 1/1971 | Quackenbush |
| 3,563,371 A | 2/1971 | Heinz |
| 3,616,898 A | 11/1971 | Massie |
| 3,708,106 A | 1/1973 | Sargent |
| 3,847,280 A | 11/1974 | Poncy |

(Continued)

FOREIGN PATENT DOCUMENTS

| | | |
|---|---|---|
| EP | 1038788 | 9/2000 |
| GB | 515876 | 12/1939 |

(Continued)

OTHER PUBLICATIONS

Jung Da Won, International Search Report in PCT/US10/33468, Jan. 13, 2011, Korean Intellectual Property Office, Daejeon, Republic of Korea, 4 pages.

(Continued)

*Primary Examiner* — Melanie Hand

(74) *Attorney, Agent, or Firm* — Florek & Endres PLLC

(57) ABSTRACT

The invention relates to a method for treating overactive bladders and a device for storing and administering non-occluded oxybutynin topical compositions.

24 Claims, 1 Drawing Sheet

(56) References Cited

U.S. PATENT DOCUMENTS

| | | |
|---|---|---|
| 3,913,789 A | 10/1975 | Miller |
| 3,926,311 A | 12/1975 | Laske |
| 3,937,396 A | 2/1976 | Schneider |
| 3,995,739 A | 12/1976 | Tasch et al. |
| 4,279,344 A | 7/1981 | Holloway, Jr. |
| 4,314,557 A | 2/1982 | Chandrasekaran |
| 4,359,506 A | 11/1982 | Wiggins et al. |
| 4,410,089 A | 10/1983 | Bortolani |
| 4,552,269 A | 11/1985 | Chang |
| 4,656,068 A | 4/1987 | Raines |
| 4,778,712 A | 10/1988 | Akao |
| 4,784,857 A * | 11/1988 | Berry et al. .................. 424/449 |
| 4,964,515 A | 10/1990 | Heyden |
| 4,998,621 A | 3/1991 | Meehan |
| 5,077,104 A | 12/1991 | Hunt et al. |
| 5,131,760 A | 7/1992 | Farmer |
| 5,164,190 A | 11/1992 | Patel et al. |
| 5,181,610 A | 1/1993 | Quick et al. |
| 5,227,169 A | 7/1993 | Heiber et al. |
| 5,253,754 A | 10/1993 | Soodak |
| 5,266,371 A | 11/1993 | Sugii et al. |
| 5,268,209 A | 12/1993 | Hunt et al. |
| 5,341,922 A | 8/1994 | Cerwin et al. |
| 5,366,296 A | 11/1994 | Stenstrom et al. |
| 5,400,808 A | 3/1995 | Turner et al. |
| 5,562,642 A | 10/1996 | Smith et al. |
| 5,601,839 A | 2/1997 | Quan et al. |
| 5,613,958 A | 3/1997 | Kochinke et al. |
| 5,633,008 A | 5/1997 | Osborne et al. |
| 5,846,558 A | 12/1998 | Nielsen et al. |
| 5,900,250 A | 5/1999 | Lee et al. |
| 5,948,433 A | 9/1999 | Burton et al. |
| 5,950,830 A | 9/1999 | Trigger |
| 6,010,715 A | 1/2000 | Wick et al. |
| 6,059,112 A | 5/2000 | Dykstra et al. |
| 6,129,929 A | 10/2000 | Wick |
| 6,159,496 A | 12/2000 | Blanchard et al. |
| 6,159,497 A * | 12/2000 | LaPrade et al. .............. 424/448 |
| 6,267,983 B1 | 7/2001 | Fujii et al. |
| 6,326,069 B1 | 12/2001 | Barnett et al. |
| 6,660,295 B2 | 12/2003 | Watanabe et al. |
| 6,676,961 B1 | 1/2004 | Lichter |
| 6,743,441 B2 | 6/2004 | Sanders et al. |
| 6,905,016 B2 | 6/2005 | Kanios et al. |
| 6,974,588 B1 | 12/2005 | Miranda et al. |
| 7,029,694 B2 | 4/2006 | Ebert et al. |
| 7,081,249 B2 | 7/2006 | Sanders et al. |
| 7,081,250 B2 | 7/2006 | Sanders et al. |
| 7,081,251 B2 | 7/2006 | Sanders et al. |
| 7,081,252 B2 | 7/2006 | Sanders et al. |
| 7,087,241 B2 | 8/2006 | Sanders et al. |
| 7,179,483 B2 | 2/2007 | Ebert et al. |
| 7,425,340 B2 | 9/2008 | Grenier et al. |
| 7,921,999 B1 | 4/2011 | Kimball |
| 2001/0009175 A1 | 7/2001 | Speckhals et al. |
| 2001/0051180 A1 | 12/2001 | Watanabe et al. |
| 2002/0168401 A1 | 11/2002 | Kanios et al. |
| 2003/0124177 A1 | 7/2003 | Ebert et al. |
| 2004/0131805 A1 | 7/2004 | Merical et al. |
| 2005/0064037 A1 | 3/2005 | Chiang |
| 2005/0214354 A1 | 9/2005 | Kanios et al. |
| 2007/0148195 A1 | 6/2007 | Ebert et al. |
| 2008/0226698 A1 | 9/2008 | Tang et al. |
| 2009/0018190 A1 | 1/2009 | Ebert et al. |
| 2011/0028814 A1 * | 2/2011 | Petersen et al. .............. 600/324 |

FOREIGN PATENT DOCUMENTS

| | | |
|---|---|---|
| GB | 1508492 | 4/1978 |
| GB | 2272877 | 6/1994 |
| JP | 54-115997 | 9/1979 |
| JP | 2000-309379 | 11/2000 |
| JP | 2004-525832 | 8/2004 |
| JP | 2005-089467 | 4/2005 |
| WO | 85/03275 | 8/1985 |
| WO | 90/05683 | 5/1990 |
| WO | 90/11065 | 10/1990 |
| WO | 93/00274 | 1/1993 |
| WO | 96/19205 | 6/1996 |
| WO | 01/80796 | 11/2001 |
| WO | 01/93683 | 12/2001 |
| WO | 02/090210 | 11/2002 |
| WO | 2004/041187 | 5/2004 |
| WO | 2004/041188 | 5/2004 |

OTHER PUBLICATIONS

Photocopy of photograph of Schwarz Pharma's Neupro (rotigoline) transdermal patch, expiration date of Dec. 2007; applicant believes this product was offered for sale prior to Dec. 21, 2006.

Simin Baharlou; International Preliminary Report on Patentability in PCT/US10/33468; Nov. 9, 2011; 6 pages; The International Bureau of WIPO; Geneva, Switzerland.

Jung Da Won; Written Opinion of the International Searching Authority in PCT/US10/33468; Jan. 13, 2011; 5 pages; Korean Intellectual Property Office; Daejon, Republic of Korea.

Van Gansbeke, "Stability of oxybutynin chloride syrup after repackaging in unit doses", American Journal of Hospital Pharmacy, Jun. 1991, vol. 48, pp. 1265-1266.

Sally Woods, "High nitrile resin at the forefront of barrier boom", Canadian Packaging, Sep. 1986, pp. 48-50.

Mitsui Toatsu Chemicals, Inc., "Acrylonitrile-type thermoplastic resin barex", Convertech, 1994, vol. 22(6):45-46.

* cited by examiner

METHOD FOR TREATING OVERACTIVE BLADDERS AND A DEVICE FOR STORAGE AND ADMINISTRATION OF TOPICAL OXYBUTYNIN COMPOSITIONS

TECHNICAL FIELD OF THE INVENTION

The present invention relates to a method for treating over active bladders and a device for storing and administering topical oxybutynin compositions. More specifically, the present invention relates to a device for storing and administering a non-occluded oxybutynin composition such as gels, creams and lotions. The device may be sized to store single or multiple doses of the topical oxybutynin composition that can be used to treat patients with over active bladders.

BACKGROUND OF THE INVENTION

Oxybutynin is an anticholinergic, antispasmodic agent that has been known since the mid 1960s and has been used for the treatment of overactive bladder and urinary incontinence. Oxybutynin has a chiral molecular center and may be present as a racemic mixture or in purified isomeric forms. Oxybutynin, as well as the purified isomeric forms, can be prepared as a free base or as a pharmaceutically acceptable salt form such as the chloride salt. Oxybutynin is metabolized to desethyloxybutynin which is believed to have pharmacological activity similar to oxybutynin.

Oxybutynin has been commercially available in the form of oral syrups, immediate release tablets, controlled release osmotic tablets and transdermal patches. Examples of oral controlled release oxybutynin formulations are disclosed in U.S. Pat. Nos. 5,674,895; 5,912,268; 6,262,115 and 6,919,092. The oral administration of oxybutynin is known to cause a number of adverse side effects. The primary adverse side effect is dry mouth, however, adverse events such as abdominal pain, dry nasal and sinus mucous membranes, constipation, diarrhea, nausea, somnolence, dizziness, impaired urination, increased post void residual volume and urinary retention have been reported.

It has been discovered that the incidences of adverse events can be reduced by the transdermal administration of oxybutynin. Transdermal oxybutynin patches are described, for example, in U.S. Pat. Nos. 5,164,190; 5,601,839; 6,743,441 and 7,081,249. Examples of non-occluded oxybutynin topical compositions are described, for example, in U.S. Pat. Nos. 7,029,694; 7,194,483 and 7,425,340. It has been reported that the transdermal administration of oxybutynin results in a reduced oxybutynin:desethyloxybutynin ratio in the plasma compared to the oral administration of oxybutynin. This reduced oxybutynin:desethyloxybutynin ratio via transdermal administration results in less adverse events.

Although oxybutynin transdermal patches and non-occluded topical compositions are known in the art and provide the benefits of oxybutynin without the increased side effects of oral administration, the development of a suitable device, container and/or packaging system for storing and administering non-occluded oxybutynin topical compositions has been problematic. Specifically, the storage and administration device needs to provide an accurate and consistent dose of oxybutynin to insure the patient receives the necessary therapeutic amounts of the drug. The device also needs to provide a stable and robust environment for the non-occluded oxybutynin topical composition. With respect to stability, the device must prevent the non-occluded oxybutynin topical composition from degrading over time, reacting with the materials forming the device and leaching or permeating through the device.

The stability of non-occluded oxybutynin topical compositions further presents many unique issues because the non-occluded oxybutynin topical compositions often contain a high solvent content, i.e., water or alcohol. The high solvent content may promote reactions with the materials forming the storage and administration device. The solvent may also evaporate, leach and/or permeate from the storage and administration device over time thereby resulting in a decreased skin flux when the non-occluded oxybutynin topical composition is dispensed and applied to a patient's skin.

Further stability complications can occur when oxybutynin chloride is employed. The large volume of solvent in the non-occluded oxybutynin topical composition will allow the oxybutynin chloride salt to disassociate, creating free chloride ions that may cause further unwanted reactions with materials forming the storage and administration device.

A device for storing and administering non-occluded oxybutynin topical compositions must also be strong, durable and useable. Specifically, the device must protect the non-occluded oxybutynin topical composition from accidentally or prematurely being dispensed or expelled from the device. For example, the device may be inadvertently squeezed, crushed or compressed during storage and transport to the patient. The device must withstand these inadvertent compressive forces without bursting but allow the patient to easily open and dispense the non-occluded oxybutynin composition.

Containers for cosmetic and pharmaceutical products such as alcohol pads, transdermal patches and perfumes are described in the art. For example, WO 90/05683 describes a heat sealed sachet that can be used to store cosmetic and pharmaceutical materials wherein the layers of the sachet can be peeled apart to allow access to the stored material without touching the stored material. This structure would not be useful for a non-occluded oxybutynin topical composition because the sealing bond strength is low and may causing unwanted bursting.

Another container is disclosed in WO 85/03275 which describes a container for an alcohol preparation device that employs a fluid retaining pad sandwiched between two fluid impermeable layers. Still other flexible containers are taught in GB 515,876 as well as in U.S. Pat. Nos. 4,998,621; 5,268,209; 5,400,808; 6,326,069; and 6,905,016. These prior container systems employ support structures for stored materials.

None of these prior containers suggest their use with a non-occluded oxybutynin topical composition, and, more importantly, a way to overcome the stability, strength and durability issues encountered when preparing a device for storing and administering a non-occluded oxybutynin topical composition.

It is an object of the present invention to provide a device for storing and administering a non-occluded oxybutynin topical composition that can provide an accurate and consistent dose of oxybutynin to a patient.

It is a further object of the present invention to provide a device for storing a non-occluded oxybutynin topical composition that provides a stable environment for the non-occluded oxybutynin topical composition for at least one year or longer.

It is another object of the present invention to provide a device for storing and administering a non-occluded oxybutynin topical composition that is strong, durable and robust to avoid unwanted and accidental ruptures or bursts under pressure of at least 20 pounds, preferably at least 25 pounds and most preferably at least 30 pounds of pressure or more.

It is still a further object of the present invention to provide a device for storing and administering a non-occluded oxybutynin topical composition that is easy to manufacture and is free of any rigid structural support mechanisms.

It is yet another object of the present invention to provide a device for storing and administering a non-occluded oxybutynin topical composition that is easy to open and from which the non-occluded oxybutynin topical composition is easily dispensed.

It is still another object of the present invention to treat human patients suffering from overactive bladder by providing to a patient a single or daily dose of a therapeutically effective amount of a non-occluded oxybutynin topical composition in a flexible storage device, removing or dispensing the single or daily dose of the non-occluded oxybutynin composition from the flexible storage device and topically applying the single or daily dose of the non-occluded oxybutynin composition to the patient's skin.

These and other objects of the present invention will become apparent from a review of the appended specification.

SUMMARY OF THE INVENTION

The present invention accomplishes the above objects and others by creating a device or a flexible container such as a pouch or sachet that is formed from a laminate material comprising, from inside out, a first polymer layer, an adhesive layer and a metal foil layer wherein the adhesive layer adheres the first polymer layer to the metal foil layer. The laminate may further comprise additional layers. The additional layers may be polymeric, paper or adhesive layers and may be between the first polymer layer and the metal foil layer or on the outer surface (away from the oxybutynin composition) of the metal foil layer. One embodiment of the present invention will further comprise an outer printing layer that will allow the device to be printed or embossed with descriptive, decorative and/or instructional information.

The first polymer layer will be in direct contact with the non-occluded oxybutynin composition and should comprise a polymer or copolymer that is substantially inert to the oxybutynin composition. Examples of materials that may be used to form the first polymer layer include, but are not limited to, polyethylene and acrylic based polymers or copolymers such as a methyl acrylate or acrylic acid.

The metal foil layer will provide a vapor barrier for the device and prevent the evaporation of the solvents from the non-occluded oxybutynin composition stored in the device. The metal foil should also prevent the permeation of materials from the external environment into the non-occluded oxybutynin composition. An example of a useful metal foil is aluminum with a thickness of about 0.20 mils to about 0.5 mils.

The device may be prepared by bringing two sheets of the laminate together so the first polymer layers are in contact (opposing), forming a reservoir for the non-occluded oxybutynin composition, placing the non-occluded oxybutynin composition into the reservoir and sealing the device. In one embodiment of the present invention, the steps of forming the reservoir and sealing the device are accomplished by heat sealing.

The device may also be prepared by folding the laminate so the first polymer layer comes into opposing contact, sealing two of the open edges of the folded structure thereby creating a reservoir for the non-occluded oxybutynin composition, placing the non-occluded oxybutynin composition into the reservoir and sealing the final (open or fill) edge of the folded structure.

After the device is prepared, i.e. filled with a non-occluded oxybutynin composition and sealed, it should provide a safe, durable and stable environment for the non-occluded oxybutynin composition for at least one year, preferably 18 months, most preferably 24 months or longer. The final prepared device should also allow a patient in need of oxybutynin therapy to easily open the device and dispense an accurate and consistent dose of the non-occluded oxybutynin composition for topical administration. The opening of the prepared device by the patient may be facilitated by notching or partially scoring a section of one of the sealed edges.

DETAILED DESCRIPTION OF THE INVENTION

As used herein, the terms "device" and "container" are used interchangeably and are broadly defined to refer to any flexible packaging system such as a sachet or pouch that is designed to hold, store and transport an accurate and reproducible amount of a non-occluded oxybutynin topical composition. In one embodiment of the present invention, the device or container should contain an amount of a non-occluded topical oxybutynin composition that will provide a single daily therapeutic dose or a multiple therapeutic dose of oxybutynin. For example, in one embodiment of the present invention the device or container may contain 0.25 g to about 5 grams of a non-occluded topical oxybutynin gel wherein about 3% to about 15% based upon the total weight of the gel is oxybutynin.

As used herein, the term "oxybutynin" refers to oxybutynin in its free base form as well as pharmaceutically acceptable salts thereof. It also includes racemic mixtures or purified isomeric forms of the free base and pharmaceutically acceptable salts thereof.

The term "topical" means a composition suitable for direct application to a skin surface and from which a therapeutically effective amount of the oxybutynin is released for transdermal administration to a patient in need of oxybutynin therapy. Examples of topical compositions include, but are not limited to, gels, lotions and creams.

The term "non-occluded" as used herein refers to a composition applied to the skin without the use of a supporting structure. In other words, a non-occluded topical composition is directly applied to the skin in a free form, which is sufficient to effect transdermal delivery of oxybutynin without the use of a support structure such as a backing member typically used for transdermal patches.

Figure 1:
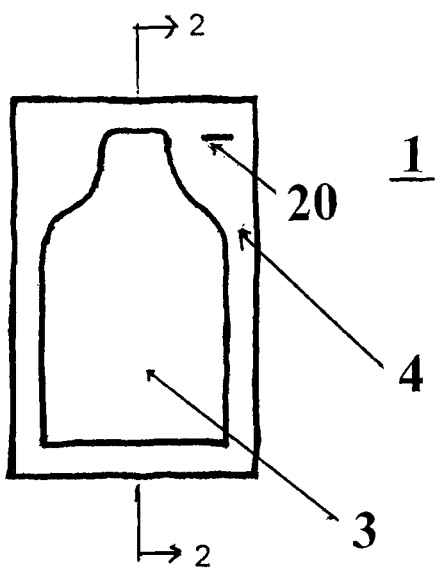
FIG. 1 is a top planar view of one embodiment of the present invention.
Figure 2:
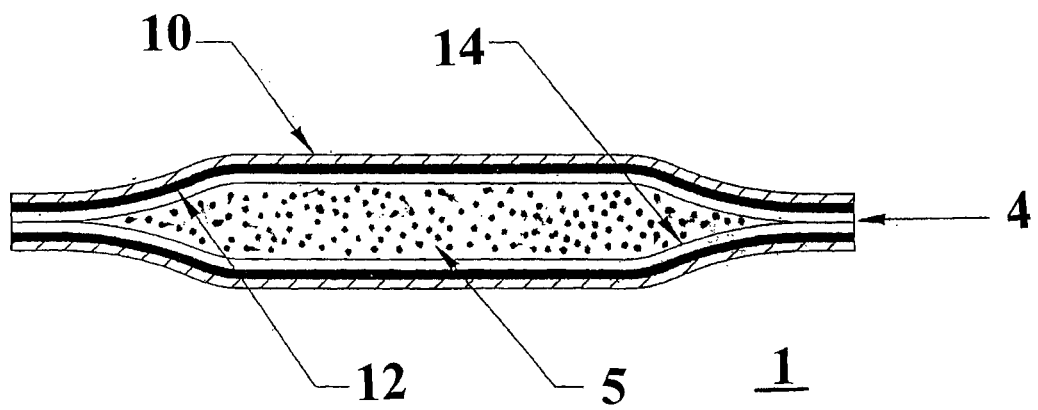
FIG. 2 is cross sectional view of the embodiment of the present shown in FIG. 1 taken along line 2-2 of FIG. 1.

Referring to FIGS. 1 and 2, the device 1, in accordance with the present invention, comprises a laminate that is processed to form a reservoir 3 for the non-occluded oxybutynin composition 5. The reservoir 3 may be prepared by joining or sealing two sheets of opposing laminate material along all its edges 4 or from a single sheet of the laminate that has been folded into an opposing structure and sealed along its edges 4. The device 1 may be in any design, shape or form, irregular or uniform. Uniform shapes such as squares, rectangles, circles and ovals are preferred in order to facilitate the sealing and manufacturing processes. The dimensions of the device 1 will be designed so the reservoir 3 can easily accommodate the desired amount of the non-occluded oxybutynin composition 5.

As shown in FIG. 1, the reservoir 3 may be formed with a narrowed or conical region to allow the dispensing of the non-occluded oxybutynin composition 5 from the device is a uniform, narrow and consolidated stream. The device 1 may also contain one or more notches 20 that will allow the user to open the device 1 and dispense the non-occluded oxybutynin composition 5 from the device 1 for application to a patient's skin. The notch 20 may be a horizontal or angular slit formed into one or more of the edges of the device. The notch 20 may also be formed by removing a portion of the laminate along the sealed edges.

The sealing of the edges of the device 1 can be accomplished by heat, ultrasound, laser, or adhesive and the like. One embodiment of the present invention employs a self-sealing mechanism (i.e., able to form a stable bond between two facing surfaces of the same material without the use of an adhesive). An example of an acceptable self-sealing mechanism is heat sealing. The seal may be a destructive seal which means the seal should form a bond whose strength equals or exceeds the bond strength of the bond joining the layers of the laminated.

The seal strength can be determined by use of a motorized test stand which slowly squeezes the finished device between two platens. An inadequate seal will be evident if the non-occluded oxybutynin composition 5 is forced out of the sealed or finished device 1 at a pressure lower than 20 pounds. An acceptable seal should with stand pressure of at least 20 pounds, preferably at least 30 pounds and most preferably at least 50 pounds without bursting. One embodiment of the present invention is able to withstand 20 to 100 pounds of pressure without bursting, preferably 25 to 80 pounds of pressure without bursting and most preferably 30 to 75 pounds of pressure without bursting. These pressures simulate the effect of pressures experienced during routine handling in packaging and patient use.

The laminate used in preparing the present invention should comprise a first polymer layer 14 that will contact the non-occluded oxybutynin composition and a metal foil layer 10 bonded to the first polymer layer 14. The first polymer layer 14 may be a thermoplastic polymer that does not substantially absorb, react with, or otherwise adversely affect the oxybutynin or other excipients or components used in the non-occluded oxybutynin composition 5. Examples of a thermoplastic material that can be used for the first polymer layer 14 are nitrile rubber modified acrylonitrile-methyl acrylate copolymers. Such materials are disclosed, for example, in U.S. Pat. No. 3,426,102, and are commercially sold under the trademark BAREX®. Another thermoplastic polymer that may be used as the first polymer layer is a polyethylene polymer or copolymer. Examples of suitable polyethylene polymers include, but are not limited to, low density polyethylene (LDPE) and linear low density polyethylene (LLDPE).

The thickness of first polymer layer 14 may be about 0.5 mil to about 2.5 mil, more preferably from about 0.75 mil to about 1.5 mil, and even more preferably from about 1.0 mil to about 1.5 mil. While thinner and thicker widths may be employed, the first polymer layer 14 should not be so thin so as to compromise its permeation and stabilizing properties, nor so thick so as to adversely affect its self-sealing and packaging properties.

The first polymer layer 14 is adhered or attached to the metal foil layer 10, such as aluminum foil, by any technique known in the art. Attachment by means of heat fusion or an adhesive layer 12, are preferred. Use of an adhesive layer 12 is preferred in order to achieve greater tear resistance properties which are desirable in creating child resistant/proof packaging.

Suitable adhesives that may be used to adhere or bind the first polymer layer 14 to the metal foil layer 10 include, but are not limited to, urethanes and ethylene/acrylic acid copolymers. Other examples of suitable adhesive materials are described in U.S. Pat. Nos. 4,359,506 and 5,268,209. The adhesive 12 should be selected so it creates a destructive bond between the metal foil layer 10 and the first polymer layer 14. The adhesive may be applied to metal foil and dried to a thickness that should preferably not exceed about 1 mil, and is preferably in a range from about 0.3 mil to about 0.75 mil.

The metal foil layer 10 may be a thickness of about 0.20 mil to about 0.50 mil, preferably about 0.25 mil to about 0.40 mil.

The laminate employed in the present invention may comprise additional layers between the first polymer layer 14 and the metal foil layer 10 and/or on outer or external surface of the metal foil layer 10. The additional layers may provide additional strength and stability to the device 1. One embodiment of the present invention includes an additional external layer such as a paper or polymeric layer that will allow printing or embossing of indicia onto the outer most surface of the device.

Examples of non-occluded oxybutynin composition 5 that may be used in the present invention are described in U.S. Pat. No. 7,179,483, and in particular examples 3-21, which are incorporated herein by reference. Additional examples of non-occluded oxybutynin compositions that may be used in the present invention are described in U.S. Pat. No. 7,425,340.

One embodiment of the present invention is designed for use with a non-occluded oxybutynin gel composition, preferably an oxybutynin chloride gel. The gel comprises oxybutynin or a pharmaceutically acceptable salt thereof, a solvent and a thickening agent.

The oxybutynin is present in the gel in an amount of about 2% to about 20% based upon the total weight of the gel, preferably about 4% to about 15% based upon the total weight of the gel and most preferably about 8% to about 12% based upon the total weight of the gel.

The solvent should comprise at least 50% of the total weight of the gel, preferably at least 60% or more of the total weight of the gel and most preferably at least 70% or more based upon the total weight of the gel. The solvent preferably is an organic solvent or a mixture of water and an organic solvent. The organic solvent should be safe when applied to the human skin and have a relatively low boiling point, i.e., less than 100° C., to allow the quick evaporation when the gel is applied to a patient's skin. Examples of organic solvents that are useful in creating gels for use with the present invention include $C_1$ to $C_6$ hydrocarbons, preferably $C_1$ to $C_6$ alcohols such as methanol, ethanol, isopropyl alcohol, benzyl alcohol, propanol and mixtures thereof. If a water:organic solvent mixture is employed as the solvent for the oxybutynin gel, the ratio of water to organic solvent should range from about 1:2 to about 1:20, preferably about 1:3 to about 1:12 and most preferably about 1:5 to about 1:10.

One embodiment of the present invention employs a non-occluded oxybutynin gel composition that comprises at least 50% of the total weight of the gel of a volatile organic solvent, preferably at least 60% or more of the total weight of the gel of a volatile organic solvent and most preferably at least 65% or more based upon the total weight of the gel of a volatile organic solvent.

The thickening agent may be a compound of high molecular weight which acts to produce a semisolid, viscous solution or suspension-type formulation. The thickening agent may be hydrophobic or hydrophilic and is generally a polymer.

Examples of suitable thickening agents for use in the present invention may include synthetic polymers, vinyl polymers, cellulose polymers, natural occurring gelling agents and mixtures of the foregoing. In one embodiment of the present invention, the thickening agent should exhibit a viscosity of about 1,000 cps to 500,000 cps, preferably 5,000 cps to 250 cps and most preferably about 10,000 cps to 100,000 cps when a 2% aqueous solution of the thickening agent is prepared.

Examples of synthetic polymers that may be used as thickening agents include polyacrylic acids or poly(1-carboxyethylene), carboxypolymethylenes prepared from acrylic acid cross-linked with allyl ethers of (polyalkyl) sucrose or pentaerythritol (e.g. CARBOPOL® 940/941/980/981/1342/1382 and carbamer polymers such as carbomer 934P/974P), sodium acrylate polymers (e.g. AQUAKEEP™ J-550/J-400), other polycarboxylic acids and alkyl acrylate polymers (e.g. PEMULEN®).

Examples of the vinyl polymers that may be used as thickening agents include carboxyvinyl polymers, polyvinyl pyrrolidone, polyvinyl alcohol, polyvinyl methyl ether, polyvinyl ether and polyvinyl sulfonates.

Examples of cellulose polymers that may be used as thickening agents include hydroxypropyl cellulose, hydroxypropylmethyl cellulose, hydroxypropylethyl cellulose, hydroxypropylbutyl cellulose, hydroxypropylpentyl cellulose, hydroxyethyl cellulose, ethylcellulose, carboxymethyl cellulose and cellulose acetate.

Examples of natural gelling agents that may be used as thickening agents include, dextran, gaur-gum, tragacanth, xanthan gum, sodium alginate, sodium pectinate, acacia gum, Irish moss, karaya gum, guaiac gum, locust bean gum, etc., while natural high molecular weight compounds include, among others, various proteins such as casein, gelatin, collagen, albumin (e.g. human serum albumin), globulin, fibrin, etc. and various carbohydrates such as cellulose, dextrin, pectin, starches, agar, mannan, and mixtures of the foregoing.

Additional compounds that may be used as thickening agents are polyethylene compounds (e.g. polyethylene glycol, etc.), polysaccharides (e.g., polysucrose, polyglucose, polylactose, etc.) and salts thereof, acrylic acid esters, alkoxybutyninpolymers (e.g., polyoxyethylene-polyoxypropylene copolymers such as the PLURONIC® line of BASF, Parsippany, N.J.), polyethylene oxide polymers, polyethers, gelatin succinate, colloidal magnesium aluminum silicate (which may be useful as a gel stabilizer in conjunction with another gelling agent) and petroleum jelly.

The amount of thickening agent employed in a gel for use with the present invention may vary depending on the specific result to be achieved. However, in one aspect, the amount of gelling agent may be from about 0.05% to about 10%, preferably about 0.1% to about 5 wt % and most preferably about 0.1% to about 3 wt % based upon the total weight of the non-occluded oxybutynin composition.

The amount of thickening agent employed in the non-occluded oxybutynin composition should impart a viscosity to the non-occluded oxybutynin composition of about 1,000 cps to about 200,000 cps, preferably about 2,500 cps to about 100,000 cps and most preferably about 5,000 cps to about 75,000 cps.

A non-occluded oxybutynin gel composition useful in the present invention may also optionally comprise up to about 10 wt % of a lipophilic or hydrophobic agent, which may serve as an emollient or anti-irritant. Emollients and anti-irritants suitable for use in the present invention may include lipophilic agents such as, but not limited to, fatty materials such as fatty alcohols of about 12 to 20 carbon atoms, fatty acid esters having about 12 to 20 carbon atoms in the fatty acid moiety, petrolatum, mineral oils, and plant oils such as soybean oil, sesame oil, almond oil, aloe vera gel, glycerol, and allantoin.

A non-occluded oxybutynin gel composition useful in the present invention may also comprise a pH adjusting agent. The pH adjusting agent may help reduce irritation and/or aid in obtaining proper gelling. Examples of some pH adjusting agents that may be used include, but are not limited to, organic amines (e.g., methylamine, ethylamine, di/trialkylamines, alkanolamines, dialkanolamines, triethanolamine), carbonic acid, acetic acid, oxalic acid, citric acid, tartaric acid, succinic acid or phosphoric acid, sodium or potassium salts thereof, hydrochloric acid, sodium hydroxide, ammonium hydroxide, potassium hydroxide and mixtures thereof. The pH of the non-occluded oxybutynin gel composition should be about 4 to about 11, preferably about 4.5 to about 9 and most preferably about 5 to about 7.

The non-occluded oxybutynin gel composition that may be used in the present invention may further comprise conventional processing and aesthetic aids such as chelating agents, surfactants, permeation enhancers, preservatives, anti-microbial agents, antibacterial agents, antioxidants, lubricants and mixtures of any of the foregoing. A more detailed discussion of these conventional processing and aesthetic aids can be found in U.S. Pat. No. 7,179,483 which is incorporated herein by reference.

The device for storing and administering a non-occluded oxybutynin topical composition prepared in accordance with the present invention should prevent the non-occluded oxybutynin topical composition from degrading when stored for at least one year, preferably two years or longer. For example, the device when filled with the non-occluded oxybutynin composition and sealed can be stored for 26 weeks, 52 weeks, 104 weeks or longer without exhibiting any adverse effect on the non-occluded oxybutynin composition such as a substantially loss of solvent, substantial change in pH or degradation of the oxybutynin. After storage the device should also be able to with stand pressure of at least 20 pounds, preferably at least 30 pounds and most preferably at least 50 pounds without bursting.

One embodiment of the present invention will allow the non-occluded oxybutynin topical composition to be stored at 25° C. and 60% relative humidity for twenty-six (26) weeks. After storage for 26 weeks in the sealed device, the non-occluded oxybutynin composition should exhibit the parameters described in TABLE 1.

TABLE 1

| Parameter | Preferred | More Preferred | Most Preferred |
|---|---|---|---|
| Oxybutynin Content | 90-110% of labeled claim | 90-110% of labeled claim | 90-110% of labled claim |
| PCGE | NMT 0.2% | NMT 0.15% | NMT 0.1% |
| PCGA | NMT 2.0% | NMT 1.0% | NMT 0.5% |
| Individual Unknown | NMT 0.2% | NMT 0.175% | NMT 0.15% |
| Total Unknown | NMT 1.0% | NMT 0.75% | NMT 0.5% |
| Solvent | NMT 20% change | NMT 15% change | NMT 10% change |
| pH | NMT 1 pH change | NMT 0.75 pH change | NMT 0.5 pH change |

NMT is Not More Than
PCGE is Phenylcyclohexyl glycolic acid ethyl ester, also known as ethylphenyl-cyclohexyl glycolate, cyclohexylphenyl-glycolic acid, and cyclohexyl-mandelic acid ethyl ester.
PCGA is USP Oxybutynin Related Compound A, also known as Phenylcyclohexylglycolic acid, cyclohexylmandelic acid, oxybutacide, CHMA.

With respect to the change in solvent, the above TABLE 1 indicates the change in solvent after storage should not vary by more than 20%, 15% or 10% of the initial amount of solvent. This means, if the initial amount of solvent was 100 mg of ethanol, after storage under the appropriate time and conditions, the amount of solvent should not be less than 80 mg, 85 mg or 90 mg respectively. Similarly, with respect to the change in pH, if the initial pH of the non-occluded oxybutynin topical composition is 6, after storage, the pH should be no lower than 5 and no higher than 7 for the NMT 1 pH criteria and should not be lower than 5.5 or higher than 6.5 for the NMT 0.5 pH criteria.

Another embodiment of the present invention will allow the non-occluded oxybutynin topical composition to be stored at 25° C. and 60% relative humidity for fifty-two (52) weeks. After storage for 52 weeks in the sealed device, the non-occluded oxybutynin composition should exhibit the parameters described in TABLE 2.

TABLE 2

| Parameter | Preferred | More Preferred | Most Preferred |
|---|---|---|---|
| Oxybutynin Content | 90-110% of labeled claim | 90-110% of labeled claim | 90-110% of labeled claim |
| PCGE | NMT 0.2% | NMT 0.17% | NMT 0.15% |
| PCGA | NMT 2.0% | NMT 1.7% | NMT 1.0% |
| Individual Unknown | NMT 0.2% | NMT 0.18% | NMT 0.16% |
| Total Unknown | NMT 1.0% | NMT 0.80% | NMT 0.65% |
| Solvent | NMT 20% change | NMT 15% change | NMT 10% change |
| pH | NMT 1 pH change | NMT 0.75 pH change | NMT 0.5 pH change |

A further embodiment of the present invention will allow the non-occluded oxybutynin topical composition to be stored at 25° C. and 60% relative humidity for one hundred four (104) weeks. After storage for 104 weeks in the sealed device, the non-occluded oxybutynin composition should exhibit the parameters described in TABLE 2.

A still further embodiment of the present invention will allow the non-occluded oxybutynin topical composition to be stored at 40° C. and 75% relative humidity for thirteen (13) weeks. After storage for 13 weeks in the sealed device, the non-occluded oxybutynin composition should exhibit the parameters described in TABLE 3.

TABLE 3

| Parameter | Preferred | More Preferred | Most Preferred |
|---|---|---|---|
| Oxybutynin Content | 90-110% of labeled claim | 90-110% of labeled claim | 90-110% of labeled claim |
| PCGE | NMT 0.2% | NMT 0.15% | NMT 0.1% |
| PCGA | NMT 2.0% | NMT 1.0% | NMT 0.5% |
| Individual Unknown | NMT 0.2% | NMT 0.175% | NMT 0.15% |
| Total Unknown | NMT 1.0% | NMT 0.75% | NMT 0.5% |
| Solvent | NMT 20% change | NMT 15% change | NMT 10% change |
| pH | NMT 1 pH change | NMT 0.75 pH change | NMT 0.5 pH change |

An additional embodiment of the present invention will allow the non-occluded oxybutynin topical composition to be stored at 40° C. and 75% relative humidity for twenty-six (26 weeks). After storage for 26 weeks in the sealed device, the non-occluded oxybutynin composition should exhibit the parameters described in TABLE 4.

TABLE 4

| Parameter | Preferred | More Preferred | Most Preferred |
|---|---|---|---|
| Oxybutynin Content | 90-110% of labeled claim | 90-110% of labeled claim | 90-110% of labeled claim |
| PCGE | NMT 0.2% | NMT 0.17% | NMT 0.15% |
| PCGA | NMT 2.0% | NMT 1.7% | NMT 1.0% |
| Individual Unknown | NMT 0.2% | NMT 0.18% | NMT 0.16% |
| Total Unknown | NMT 1.0% | NMT 0.80% | NMT 0.65% |
| Solvent | NMT 20% change | NMT 15% change | NMT 10% change |
| pH | NMT 1 pH change | NMT 0.75 pH change | NMT 0.5 pH change |

Due to the high solvent content of the non-occluded oxybutynin compositions used in the present invention there is a chance that material from the laminate forming the device may leach from the laminate into the non-occluded oxybutynin composition. This leaching effect is undesirable and should be kept to a minimum or eliminated completely. In order to avoid the unwanted leaching of laminate compounds into the non-occluded oxybutyinin composition, the laminate should be selected so upon storage of the filled and sealed device, the total amount of leachable materials is not more than 1% of the total weight of the non-occluded oxybutynin composition. More importantly, after storage of the filled and sealed device, no individual leachable material should exceed the acceptable daily intake limits established by the United States Food and Drug Administration.

One embodiment of the present invention, such as an LLDPE device, will allow the total leachable concentration in the non-occluded oxybutynin composition after storage in a filled and sealed device for 52 weeks at 25° C. and 60% relative humidity to be not more than 300 ppm, preferably not more than 200 ppm and most preferably not more than 150 ppm.

Another embodiment of the present invention, such as an LLDPE device, will allow the total leachable concentration in the non-occluded oxybutynin composition after storage in a filled and sealed device for 104 weeks at 25° C. and 60% relative humidity to be not more than 300 ppm, preferably not more than 200 ppm and most preferably not more than 150 ppm.

A further embodiment of the present invention, such as a BAREX® device, will allow the total leachable concentration in the non-occluded oxybutynin composition after storage in a filled and sealed device for 52 weeks at 25° C. and 60% relative humidity to be not more than 100 ppm, preferably not more than 50 ppm and most preferably not more than 25 ppm.

A still further embodiment of the present invention, such as a BAREX® device, will allow the total leachable concentration in the non-occluded oxybutynin composition after storage in a filled and sealed device for 104 weeks at 25° C. and 60% relative humidity to be not more than 100 ppm, preferably not more than 50 ppm and most preferably not more than 25 ppm.

The "leachable" materials are determined by first conducting an extraction study on samples of the laminate and samples of the first polymer layer of the laminate (14) to identify potential leachable components. Once the potential leachable components are identified, the storage and administration device is filled with an appropriate dose of the non-occluded oxybutynin composition and sealed. The filled and sealed device is stored at 25° C. and 60% relative humidity for the required time period. After storage, the device is opened and the non-occluded oxybutynin composition is analyzed using an appropriate analytical technique such as high performance liquid chromatography (HPLC).

The initial extraction study to determine the potential leachable components may be conducted by placing a sample of the laminate and/or sample of the first polymer layer in a Soxhlet extraction apparatus or an open bottle along with a suitable solvent such as alcohol, water or alcohol and water mixtures. The solvent is then analyzed by gas chromatography/mass spectroscopy (GCMS); high performance liquid chromatography (HPLC) or liquid chromatography/mass spectroscopy (LCMS) to determine the identity of any potential leachable compound.

The present invention also relates to a method for treating human patients suffering from overactive bladder comprising the steps of: a) providing a storage and administration device comprising a single or daily dose of a non-occluded oxybutynin composition to a human; b) dispensing the single or daily dose of the oxybutynin composition from the storage and administration device; and c) applying the single or daily dose of the oxybutynin composition to the skin of the human patient, such as the abdomen, thighs, arms or combination of the foregoing.

The storage and administration device employed in the above described method may be a pouch or sachet as described previously and is prepared from a laminate material comprising, from inside out, a first polymer layer (14), an adhesive (12) and a metal foil layer (10) wherein the adhesive layer (12) adheres the first polymer layer (14) to the metal foil layer (10).

The non-occluded oxybutynin composition is dispensed from the storage and administration device by opening or unsealing at least a portion of one of the device's sealed edges and applying pressure to an end of the device that is opposite of the opened or unsealed portion to force the contents of the reservoir from the device. Once the non-occluded oxybutynin composition is dispensed from the reservoir of the device, the device should be disposed.

The non-occluded oxybutynin composition 5 employed in the above described method may be a gel, cream or lotion as previously described. One embodiment of the method of the present invention employs an oxybutynin gel that comprises oxybutynin or a pharmaceutically acceptable salt thereof, a solvent and a thickening agent as described previously. The amount of non-occluded oxybutynin composition in the device for the single or daily dose should comprise about 0.25 grams to about 5 grams of which about 3% to about 15% based upon total weight of the composition is oxybutynin.

DESCRIPTION OF THE PREFERRED EMBODIMENTS

The following are provided by way of example only and are by no means intended to be limiting.

EXAMPLE 1

Oxybutynin 10% Gel

A non-occluded oxybutynin chloride gel was prepared with the following composition:

| Component | % by Weight | Grams per dose |
|---|---|---|
| Oxybutynin chloride | 10.0 | 0.100 |
| Purified Water, USP | 10.5 | 0.105 |
| Alcohol, USP | 73.3 | 0.733 |
| Glycerin, USP | 1.0 | 0.010 |
| Sodium Hydroxide Solution, 2N | 3.2 | 0.032 |
| Hydroxypropyl Cellulose, NF (KLUCEL ® HF) | 2.0 | 0.020 |
| Total | 100 | 1.0 |

The above composition was prepared by mixing the alcohol, oxybutynin chloride and glycerin in a jacketed mixer for about 5 minutes. The KLUCEL® HF was slowly added while continuing to mix. The water and sodium hydroxide solution are added to obtain a pH of about 6. After all ingredients were added, the mixing continued for 1.5 to 3 hours. The temperature of the mixer was maintained between 15-35° C.

EXAMPLE 2

Oxybutynin 4.4% Gel

A non-occluded oxybutynin chloride gel was prepared according to the procedure described in Example 1 to produce the following composition:

| Component | % by Weight | Grams per dose |
|---|---|---|
| Oxybutynin chloride | 4.40 | 0.132 |
| Purified Water, USP | 18.0 | 0.540 |
| Alcohol, USP | 73.3 | 2.199 |
| Glycerin, USP | 1.0 | 0.030 |
| Sodium Hydroxide Solution, 2N | 1.3 | 0.039 |
| Hydroxypropyl Cellulose, NF (KLUCEL ® HF) | 2.0 | 0.060 |
| Total | 100 | 3.0 |

EXAMPLE 3

Oxybutynin 13.2% Gel

A non-occluded oxybutynin hydrochloride gel was prepared according to the procedure described in Example 1 to produce the following composition:

| Component | % by Weight | Grams per dose |
|---|---|---|
| Oxybutynin chloride | 13.2 | 0.132 |
| Purified Water, USP | 5.90 | 0.059 |
| Alcohol, USP | 73.3 | 0.733 |
| Glycerin, USP | 1.0 | 0.010 |
| Sodium Hydroxide Solution, 2N | 4.6 | 0.046 |
| Hydroxypropyl Cellulose, NF (KLUCEL ® HF) | 2.0 | 0.020 |
| Total | 100 | 1.0 |

EXAMPLE 4

A device in accordance with the present invention was prepared using a BAREX® laminate that had the following composition from inside (oxybutynin contact) the device to outside: 1.5 mil BAREX®/adhesive/0.35 mil aluminum foil/ 81b LDPE/white 261b C1S paper. The BAREX® resin is an acrylonitrile-methyl acrylate copolymer. The BAREX® laminate was commercially available from Graphic Packaging International, Inc. of Shaumburg, Ill., USA under the designation LC FLEX No. 81920 (formerly S-6037).

A Klockner LA-160 Packager machine was set up using a single roll of the BAREX® laminate. The laminate was 12 inches wide and slit into two halves. The two halves were guided together such that the BAREX® resin sides of the two halves opposed each other. The two 6 inch webs were then heat sealed together to form three lanes of 3-sided sachets.

The oxybutynin chloride gel of Example 1 was delivered into each sachet using individually-adjustable, precision metering pumps (one for each lane). The pumps were primed by applying nitrogen pressure to the pressure/storage vessel. After priming, each pump delivered approximately 1 gram of the oxybutynin chloride gel of Example 1 to each reservoir of the 3-sided sachets. The final side of each sachet was then heat sealed. The three sachets were then split apart and cut into individual sachets.

The cycle or web speed and sealing temperatures will depend upon the machines and equipment employed. In this Example, a longitudinal heat seal temperature of about 150° C. (145-155° C.), a cross heat seal temperature of about 150° (145-155° C.) and a cycle speed of 30-50 cycles per minute were employed.

The 1 g sachets prepared in this Example were tested using a motorized test stand which slowly squeezed the sachets between two platens. The 1 g sachets received 30 and 50 pounds of pressure without bursting.

The sachets prepared in this Example were also subjected to stability testing at 25° C. and 60% relatively humidity for at least 26 and 52 weeks and 40° C. and 75% relatively humidity for at least 13 and 26 weeks. The samples exhibited a stability that met the preferred, more preferred and most preferred values contained in TABLES 1-4 above.

EXAMPLE 5

A device in accordance with the present invention was prepared using a BAREX® laminate that had the following composition from inside (oxybutynin contact) the device to outside: 1.5 mil BAREX®/adhesive/0.35 mil aluminum foil/ 81b LDPE/white 261b C1S paper. The BAREX® resin is an acrylonitrile-methyl acrylate copolymer. The BAREX® laminate was commercially available from Graphic Packaging International, Inc. of Shaumburg, Ill., USA under the designation LC FLEX No. 81920 (formerly S-6037).

1 gram sachets using the oxybutynin chloride composition of Example 1 were prepared according to the procedure described in Example 4 with a longitudinal heat seal temperature of 165-180° C., a cross heat seal temperature of 165-180° C. and a cycle speed of 50-60 cycles per minute were employed.

The 1 g sachets prepared in this Example were tested using a motorized test stand which slowly squeezed the sachets between two platens. The 1 g sachets received 30 pounds of pressure without bursting.

EXAMPLE 6

A device in accordance with the present invention was prepared using an LLDPE laminate that had the following composition from inside (oxybutynin contact) the device to outside: LLDPE/EAA (ethylene/acrylic acid copolymer) resin/0.35 mil aluminum foil/white primacor resin blend/water-base extrusion primer/proprietary treat process/polyester. The LLDPE laminate was commercially available from Alcoa Flexible Packaging of Richmond, Va. under the name PHARMA POUCH PP 1312.

1 gram sachets using the oxybutynin chloride composition of Example 1 were prepared according to the procedure described in Example 4 with a longitudinal heat seal temperature of about 130° C. (125-135° C.), a cross heat seal temperature of about 130° C. (125-135° C.) and a cycle speed of about 23 (20-26) cycles per minute.

The 1 g sachets prepared in this Example were tested using a motorized test stand which slowly squeezed the sachets between two platens. The 1 g sachets received 50 pounds of pressure without bursting.

The sachets prepared in this Example were also subject to stability testing at 25° C. and 60% relatively humidity for at least 26 and 52 weeks and 40° C. and 75% relatively humidity for at least 13 and 26 weeks. The samples exhibited a stability that met the preferred, more preferred and most preferred values contained in TABLES 1-4 above.

EXAMPLE 7

A device in accordance with the present invention was prepared using an LLDPE laminate that had the following composition from inside (oxybutynin contact) the device to outside: LLDPE/EAA (ethylene/acrylic acid copolymer) resin/0.35 mil aluminum foil/white primacor resin blend/water-base extrusion primer/proprietary treat process/polyester. The LLDPE laminate was commercially available from Alcoa Flexible Packaging of Richmond, Va. under the name PHARMA POUCH PP 1312.

3 gram sachets using the oxybutynin chloride composition of Example 2 were prepared according to the procedure described in Example 5 except a longitudinal heat seal temperature of about 185° C. (180-190° C.), a cross heat seal temperature of about 185° C. (180-190° C.) and a cycle speed of about 50 (45-55) cycles per minute were employed.

The 3 g sachets prepared in this Example were tested using a motorized test stand which slowly squeezed the sachets between two platens. The 3 g sachets received 100 pounds of pressure without bursting.

EXAMPLE 8

A device in accordance with the present invention was prepared using an LLDPE laminate that had the following composition from inside (oxybutynin contact) the device to outside: LLDPE/EAA (ethylene/acrylic acid copolymer) resin/0.35 mil aluminum foil/white primacor resin blend/water-base extrusion primer/proprietary treat process/polyester. The LLDPE laminate was commercially available from Alcoa Flexible Packaging of Richmond, Va. under the name PHARMA POUCH 1312.

1 gram sachets using the oxybutynin chloride composition of Example 3 were prepared according to the procedure described in Example 5 except a longitudinal heat seal temperature of about 155° C. (150-160° C.), a cross heat seal temperature of about 190° C. (185-195° C.) and a cycle speed of about 23 (20-26) cycles per minute were employed.

The 1 g sachets prepared in this Example were tested using a motorized test stand which slowly squeezed the sachets between two platens. The 1 g sachets received 50 pounds of pressure without bursting.

COMPARATIVE EXAMPLE 1

A device not in accordance with the present invention was prepared using a 2 mil LDPE laminate obtained from Tekni- Plex Inc. of Flemington, N.J. The laminate had the following composition from inside (oxybutynin contact) the device to outside: 2 mil LDPE/10.0# ethylene-acrylic acid copolymer/ 0.00035 mil aluminum foil/10.0#LDPE/26# C1S Paper. All the attempts to create an oxybutynin chloride topical gel sachet resulted in leaking pouches.

EXAMPLE 9

A leachable study was conducted on a product as described in Example 4. In the first part of the study samples of the BAREX® laminate and samples of acrylonitrile-methyl acrylate copolymer were exposed to aggressive Soxhlet and open bottle extractions using four different solvent systems: 1) 190 proof ethanol (HPLC grade); 2) 85% of 190 proof ethanol (HPLC grade) and 15% nanopure deionized water; 3) isopropanol (HPLC grade) and 4) nanopure deionized water. The extracts of the full laminate and acrylonitrile-methylacrylate copolymer were analyzed by GCMS, HPLC and LC/MS. Based upon the extraction testing the following compounds were identified as potential leachable components:
Lauryl alcohol;
Lauryl acrylate;
Nonylphenol;
Di-octyl maleate;
Di-octyl fumarate;
Butyl stearate; and
Tris-nonylphenyl phosphate The extraction study also identified nonylphenyl phosphate as a potential leachable, however, it was later determined that is compound was generated as an artifact of the hydrolytic oxidation of the tris-nonylphenyl phosphate during the analysis.

1 gram sachets prepared according to the procedure described in Example 4 were stored at 25° C. and 60% relatively humidity for 122 weeks. After storage, the contents of a sachet were transferred to a glass scintillation vial and approximately 2 g of acetonitrile was added to the mixture vortex. Samples were prepared in triplicate and analyzed by GCMS. The GCMS test results indicated the stored gel contained:
less than 1 ppm of lauryl alcohol;
less than 1 ppm of lauryl acrylate;
less than 1 ppm of nonylphenol;
less than 1 ppm of di-octyl maleate;
less than 1 ppm of di-octyl fumarate; and
less than 1 ppm of butyl stearate.

Due to the thermal instability of tris-nonylphenyl phosphate, the vortexed sample was also analyzed by HPLC and found to contain less than 1 ppm of tris-nonylphenyl phosphate.

1 gram sachets prepared according to the procedure described in Example 4 were stored at 25° C. and 60% relatively humidity for 63 and 65 weeks. After storage, the contents of a sachet were transferred to a glass scintillation vial and approximately 2 g of acetonitrile was added to the mixture vortex. Samples were again prepared in triplicate and analyzed by GCMS. The GCMS test results indicated the stored gel contained:
less than 1 ppm of lauryl alcohol;
less than 1 ppm of lauryl acrylate;
less than 1 ppm of di-octyl maleate;
less than 1 ppm of di-octyl fumarate; and
less than 1 ppm of butyl stearate.

The GCMS analysis also indicated the gel stored for 63 and 65 weeks contained between less than 1 ppm and 6.46 ppm of nonylphenol. Specifically, the tests on the 63 week sample yielded values of 1.12 ppm, 1.32 ppm and less than 1 ppm for the nonylphenol, and the tests on the 65 week sample yielded values of 6.46 ppm, 4.23 ppm and 4.68 ppm.

The vortexed sample was also analyzed by HPLC and found to contain less than 1 ppm of tris-nonylphenyl phosphate.

EXAMPLE 10

A leachable study was conducted on a product as described in Example 6. In the first part of the study samples of the PHARMA POUCH PP1312 laminate and samples of the LLDPE polymer were exposed to aggressive Soxhlet and open bottle extractions using four different solvent systems: 1) 190 proof ethanol (HPLC grade); 2) 85% of 190 proof ethanol (HPLC grade) and 15% nanopure deionized water; 3) isopropanol (HPLC grade) and 4) nanopure deionized water. The extracts of the full laminate and LLDPE polymer were analyzed by GCMS, HPLC and LC/MS. Based upon the extraction testing the following compounds were identified as potential leachable components:
Erucamide (Z-docos-13-enamide)(CAS #112-84-5);
tris-2,4-di-tert-butylphenyl phosphate (CAS #6683-19-8) (IGRAFOS 168 phosphate which is an oxidation product of Igrafos 168 known to be used by Alcoa as an antioxidant);
tris-2,4-di-tert-butylphenyl phosphite (CAS #31570-04-4) (IGRAFOS 168); and
Octadecyl 3-(3,5-di-tert-butyl-4-hydroxyphenyl)propionate (CAS #2082-79-3) (IRGANOX 1076 also known to be used by Alcoa as an antioxidant).

1 gram sachets prepared according to the procedure described in Example 6 were stored at 25° C. and 60% relatively humidity for 121 weeks, 104 weeks and 99 weeks. After storage, the contents of a sachet were transferred to a glass scintillation vial and approximately 2 g of acetonitrile was added to the mixture vortex. Samples were prepared in triplicate and analyzed by HPLC and LCMS and found to contain the following leachables:

| Sample | Erucamide | IRGAFOS 168 Phosphate | IRGANOX 1076 |
|---|---|---|---|
| 121 weeks | 26.0 ppm | 102.1 ppm | 10.82 ppm |
| 121 weeks | 23.1 ppm | 60.0 ppm | 8.06 ppm |
| 121 weeks | 21.1 ppm | 104.3 ppm | 9.59 ppm |
| 104 weeks | 23.2 ppm | 109.1 ppm | 8.61 ppm |
| 104 weeks | 17.1 ppm | 102.3 ppm | 9.55 ppm |
| 104 weeks | 29.1 ppm | 121.5 ppm | 11.50 ppm |
| 99 weeks | 16.3 ppm | 100.1 ppm | 12.81 ppm |
| 99 weeks | 21.3 ppm | 85.7 ppm | 9.37 ppm |
| 99 weeks | 23.6 ppm | 95.8 ppm | 8.96 ppm |
| average | 22.3 ppm | 97.9 ppm | 9.9 ppm |

Although IRGAFOS 168 was reported in the extraction study as a potential leachable only its oxidation product IRGAFOS 168 phosphate was measured due to the poor stability of IRGAFOS 168 in solution and its rapid conversion to IRGAFOS 168 phosphate.

While certain preferred and alternative embodiments of the present invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

The term "comprising" as used in the following claims is an open-ended transitional term that is intended to include additional elements not specifically recited in the claim. The term "consisting essentially of" as used in the following claims is a partially closed transitional phrase and is intended to include the recited elements plus any unspecified elements that do not materially affect the basic and novel characteristics of the claim. For example, an outermost layer on the disclosed laminates that are embossed or printed with indicia would be included in the meaning of "consisting essentially of", even if not specifically recited. The term "consists of" as used in the following claims is intended to indicate that the claim is restricted to the recited elements.

The invention claimed is:

1. A device for storing and administering a non-occluded oxybutynin topical composition comprising:
   a) a non-occluded oxybutynin topical composition comprising:
      i) a therapeutically effective amount of oxybutynin;
      ii) a thickening agent and
      iii) 50% or more based upon the weight of the non-occluded oxybutynin topical composition of a solvent;
   b) a reservoir for the non-occluded oxybutynin topical composition; and
   c) a laminate surrounding the reservoir and non-occluded oxybutynin topical composition comprising:
      i) a first polymer that is in contact with the non-occluded oxybutynin topical composition; and
      ii) a metal foil bound to the first polymer layer; and
         d) a notch or partial scoring of the laminate surrounding the reservoir and non-occluded oxybutynin topical composition wherein the notch or partial scoring facilitates the opening of the device for dispensing the non-occluded oxybutynin topical composition from the device; and
wherein the device can withstand 30 pounds of pressure without bursting when squeezed between two platens of a motorized test stand and when the device is stored at 25° C. and 60% relative humidity for twenty-six weeks the non-occluded oxybutynin topical composition contains not more than 0.2% of phenylcyclohexyl glycolic acid ethyl ester (PCGE); not more than 2.0% phenylcyclohexylglycolic acid (PCGA) and there is not more than a 20% change in the solvent content.

2. The device of claim 1 wherein the laminate further comprises an adhesive layer between the first polymer layer and the metal foil for bonding the metal foil to the first polymer layer.

3. The device of claim 1 wherein the laminate further comprises an additional layer for embossing or printing descriptive information.

4. The device of claim 1 wherein the non-occluded oxybutynin topical composition is a gel, cream or lotion.

5. The device of claim 4 wherein the non-occluded oxybutynin topical composition is a gel.

6. The device of claim 1 wherein the non-occluded oxybutynin topical composition comprises about 2% to about 20% based upon the total weight of the composition of oxybutynin.

7. The device as defined in claim 1 wherein the oxybutynin is oxybutynin chloride.

8. The device of claim 1 wherein the solvent comprises at least 60% of the total weight of the composition.

9. The device of claim 1 that can withstand 50 pounds of pressure without bursting.

10. The device of claim 1 that can withstand 100 pounds of pressure without bursting.

11. The device of claim 1 wherein after storage at 25° C. and 60% relative humidity for fifty-two weeks, the non-occluded oxybutynin topical composition contains not more than 0.17% of PCGE; not more than 1.7% of PCGA and there is not more than a 15% change in the solvent content.

12. The device of claim 11 wherein after storage at 25° C. and 60% relative humidity for fifty-two weeks, the non-occluded oxybutynin topical composition contains not more than 0.15% of PCGE; not more than 1.0% of PCGA and there is not more than a 10% change in the solvent content.

13. The device of claim 1 wherein after storage at 40° C. and 75% relative humidity for thirteen weeks, the non-occluded oxybutynin topical composition contains not more than 0.15% of PCGE; not more than 1.0% of PCGA and there is not more than a 15% change in the solvent content.

14. The device of claim 13 wherein after storage at 40° C. and 75% relative humidity for thirteen weeks, the non-occluded oxybutynin topical composition contains not more than 0.10% of PCGE; not more than 0.50% of PCGA and there is not more than a 10% change in the solvent content.

15. The device of claim 1 wherein after storage at 40° C. and 75% relative humidity for twenty-six weeks, the non-occluded oxybutynin topical composition contains not more than 0.17% of PCGE; not more than 1.7% of PCGA and there is not more than a 15% change in the solvent content.

16. The device of claim 15 wherein after storage at 40° C. and 75% relative humidity for twenty-six weeks, the non-occluded oxybutynin topical composition contains not more than 0.15% of PCGE; not more than 1.0% of PCGA and there is not more than a 10% change in the solvent content.

17. The device of claim 1 wherein the reservoir is formed by sealing at least one edge of the laminate.

18. The device of claim 17 wherein the reservoir is formed by sealing more than one edge of the laminate.

19. The device of claim 17 wherein the seal is a destructive seal.

20. A device for storing and administering a non-occluded oxybutynin topical composition comprising:
   a) a non-occluded oxybutynin topical composition with a pH of about 4.5 to about 9 comprising:
      i) about 2% to about 20% based upon the weight of the non-occluded oxybutynin topical composition of oxybutynin;
      ii) about 0.05% to about 10% based upon the weight of the non-occluded oxybutynin topical composition of a thickening agent; and
      iii) 50% or more based upon the weight of the non-occluded oxybutynin topical composition of a solvent;
   b) a reservoir for the non-occluded oxybutynin topical composition; and
   c) a laminate surrounding the reservoir and non-occluded oxybutynin topical composition comprising:
      i) a first polymer that is in contact with the non-occluded oxybutynin topical composition; and
      ii) a metal foil bound to the first polymer layer wherein the reservoir is created by forming at least one destructive seal on the laminate; and
   d) a notch or partial scoring of the laminate surrounding the reservoir and non-occluded oxybutynin topical composition wherein the notch or partial scoring facilitates the opening of the device for dispensing the non-occluded oxybutynin topical composition from the device and
wherein the device can withstand 50 pounds of pressure without bursting when squeezed between two platens of a motorized test stand; wherein when the device is stored at 25° C. and 60% relative humidity for twenty-six weeks, the non-occluded oxybutynin topical composition contains not more than 0.15% of phenylcyclohexyl glycolic acid ethyl ester (PCGE), not more than 1.00% of phenylcyclohexylglycolic acid (PCGA), there is not more than a 15% change in the solvent content and not more than a 0.75 change in pH; and wherein when the device is stored for thirteen weeks at 40° C. and 75% relative humidity, the non-occluded oxybutynin topical composition contains not more than 0.15% of PCGE, not more than 1.00% of PCGA, there is not more than a 15% change in the solvent content and not more than a 0.75 change in pH.

21. A method for treating human patients suffering from overactive bladder comprising the steps of
   a) providing a storage and administration device as defined in claim 1 to a human;
   b) dispensing a single or daily dose of the oxybutynin composition from the device; and
   c) applying the single or daily dose of the oxybutynin composition to a skin surface of the human patient.

22. A method for treating human patients suffering from overactive bladder comprising the steps of
   a) providing a storage and administration device as defined in claim 20 to a human;
   b) dispensing a single or daily dose of the oxybutynin composition from the device; and
   c) applying the single or daily dose of the oxybutynin composition to a skin surface of the human patient.

23. The device of claim 1 wherein the non-occluded oxybutynin topical composition does not include a backing member.

24. The device of claim 20 wherein the non-occluded oxybutynin topical composition does not include a backing member.

* * * * *